(12) United States Patent
Nabel et al.

(10) Patent No.: US 6,203,991 B1
(45) Date of Patent: Mar. 20, 2001

(54) INHIBITION OF SMOOTH MUSCLE CELL MIGRATION BY HEME OXYGENASE I

(75) Inventors: Gary J. Nabel; Elizabeth G. Nabel, both of Washington, DC (US)

(73) Assignee: The Regents of the University of Michigan, Ann Arbor, MI (US)

( * ) Notice: Subject to any disclaimer, the term of this patent is extended or adjusted under 35 U.S.C. 154(b) by 0 days.

(21) Appl. No.: 09/378,528

(22) Filed: Aug. 20, 1999

Related U.S. Application Data

(60) Provisional application No. 60/097,707, filed on Aug. 21, 1998.

(51) Int. Cl.[7] .............................. C12Q 1/68; C12N 15/63; C12N 15/88; A61K 48/00; C07H 21/04
(52) U.S. Cl. ........................... 435/6; 435/320.1; 435/458; 514/44; 536/23.1
(58) Field of Search ........................... 435/6, 320.1, 458; 514/44; 536/23.1

(56) References Cited

U.S. PATENT DOCUMENTS 6,066,333    5/2000    Willis et al. .......................... 424/464

OTHER PUBLICATIONS

Morita et al. Endothelial cell expression of vasoconstrictores and growth factors is regulated by smooth muscle cell–derived carbon monoxide. J. Clin. Invest. vol. 96:2676–2682, Dec. 1995.*

Ali et al. The use of DNA viruses as vectors for gene therapy. Gene Therapy vol. 1:367–384, Jan. 1994.*

Lee et al. Overexpression of heme oxygenase–1 in human pulmonary epithelial cells results in cell growth arrest and increased resistance to hyperoxia. PNAS vol. 93:10393–10398, Sep. 1996.*

Deramaudt et al. Gene transfer of human heme oxygenase into coronary endothelial cells potentially promotes angiogenesis. J. Cell. Biochem. vol. 68:121–127, Jan. 1998.*

Orkin et al. Report and recommendations of the panel to assess teh NIH investment in research on gene therapy, Dec. 1995.*

Marshall E Gene therapy's growing pains. Science vol. 269:1050–1055, Aug. 1995.*

Verma et al. Gene therapy—promises, problems and prospects. Nature vol. 389:239–242, Sep. 1997.*

Anderson WF Human gene therapy. Nature vol. 392:25–30, Apr. 1998.*

Abraham, Nader et al., "Adenovirus–Mediated Heme Oxygenase–1 Gene Transfer Into Rabbit Ocular Tissues," *Investigative Ophthalmology & Visual Science*, vol. 36, No. 11, pp. 2202–2210, Oct. 1995.

Morita, Toshisuke et al., "Carbon Monoxide Controls the Proliferation of Hypoxic Vascular Smooth Muscle Cells," *The Journal of Biological Chemistry*, vol. 272, No. 52, pp. 32804–32809, Dec. 26, 1997.

Nabel, Elizabeth et al., "Recombinant Gene Expression in Vivo Within Endothelial Cells of the Arterial Wall," *Science*, vol. 244, pp. 1342–1344, Jun. 16, 1989.

Nabel, Elizabeth et al., "Site–Specific Gene Expression in Vivo by Direct Gene Transfer into the Arterial Wall," *Science*, vol. 249, pp. 1285–1288, Sep. 14, 1990.

Abraham, N.G. et al., "Transfection of the human heme oxygenase gene into rabbit coronary microvessel endothelial cells: Protective effect against heme and hemoglobin toxicity," *Proc. Natl. Acad. Sci. USA*, vol. 92, pp. 6798–6802, Jul. 1995.

Duckers et al., "Protective properties of recombinant heme oxygenase 1 in vitro and in vivo in the ballon injured porcine artery," *Circulation*, vol. 98, No. 17 Suppl., pp. 1739–1740, Oct. 27, 1998, Meeting Info: 71$^{st}$ Scientific Sessions of the American Heart Association, Dallas, Texas, USA, Nov. 8–11, 1998.

Wever, Robert M.F. et al., "Atherosclerosis and the Two Faces of Endothelial Nitric Oxide Synthase," *Circulation*, 97, pp. 108–112, Jan. 1998.

Cooke, John P. et al., "Derangements of the Nitric Oxide Synthase Pathway, L–Arginine, and Cardiovascular Diseases," *Circulation*, vol. 96, No. 2, pp. 379–382, Jul. 15, 1997.

Moncada, S. et al., "Nitric oxide: Physiology, Pathophysiology, and Pharmacology," *Pharmacol Reviews*, vol. 43, No. 2, pp. 109–142, Jun. 1991.

Loscalzo, Joseph et al., "Nitric oxide and Its Role in the Cardiovascular System," *Progress in Cardiovascular Diseases*, vol. XXXVIII, No. 2, pp. 87–104, Sep./Oct. 1995.

McCoubrey, William K. et al., "Isolation and characterization of a cDNA from the rat brain that encodes hemoprotein heme oxygenase–3," *Eur.J.Biochem*, 247, pp. 725–732, 1997.

(List continued on next page.)

*Primary Examiner*—Robert A. Schwartzman
*Assistant Examiner*—William Sandals
(74) *Attorney, Agent, or Firm*—Brinks Hofer Gilson & Lion

(57) ABSTRACT

The present method provides a method for inhibiting restenosis associated with mechanical injury of a blood vessel. Human heme oxygenase I (HO1) is directly administered at the site of injury. The present inventors have discovered that carbon monoxide generated by HO1 is involved in the molecular pathogenesis of vascular proliferative disorders. By using adenoviral-mediated expression of inducible heme oxygenase 1 in primary vascular smooth muscle cells (vsmc) in vivo, the present inventors demonstrate that in vivo expression of HO1 can be used to treat restenosis.

28 Claims, No Drawings

OTHER PUBLICATIONS

Maines, Mahin D. et al., "Characterization of Two Constitutive Forms of Rat Liver Microsomal Heme Oxygenase. Only One Molecular Species of the Enzyme is Inducible," *J.Biol.Chem.*, vol. 261, No. 1, pp. 411–419, 1986.

Shibahara, Shigeki et al., "Cloning and expression of cDNA for rat heme oxygenase," *Proceedings of the National Academy of Sciences USA*, vol. 82, pp. 7865–7869, Dec. 1985.

Rotenberg, Mitch et al., "Isolation, Characterization, and Expression in *Escherichia coli* of a cDNA Encoding Rat Heme Oxygenase–2," *J.Biol.Chem.*, vol. 265, No. 13, pp. 7501–7506, May 5, 1990.

Yoshida, Tadashi et al., "Human heme oxygenase cDNA and induction of its mRNA by hemin," *Eur. J. Biochem.*, 171, pp. 457–461, Feb. 1988.

* cited by examiner

INHIBITION OF SMOOTH MUSCLE CELL MIGRATION BY HEME OXYGENASE I

RELATED APPLICATIONS

This non-provisional application claims priority to and incorporates by reference in its entirety U.S. provisional application No. 60/097,707 filed Aug. 21, 1998.

BACKGROUND OF THE INVENTION

The role of inducible second messenger gases like carbon monoxide (CO) in the pathophysiology of cardiovascular disease are not clear to date (Wever, et al., *Circulation* 97,108–112, 1998; Cooke and Dzau, *Circulation* 96, 379–382, 1997; Moncada, et al., *Pharmacol.Rev.* 43, 109–142, 1997; Loscalzo, and Welch, *Progress in Cardiovascular Diseases* 38, 87–104, 1995). The heme oxygenase system, that generates CO, consists of three isozymes identified so far: the inducible heme oxygenase I (HO-1), the constitutive expressed HO-2 and HO-3(Moncada, et al, *Pharmacol.Rev.*43, 109–142, 1997; McCoubrey et al., *Eur-.J.Biochem* 247, 725–732, 1997; Maines, et al., *J.Biol.Chem.* 261, 411–419, 1986; Shibahara et al., *Proceedings of the National Academy of Sciences USA* 240, 7865–7869, 1985; Rotenberg et al., *J.Biol.Chem.* 265, 7501–7506, 1990), which all catalyze oxidation of heme into the biologically active molecules iron, biliverdin and CO.

The widespread expression of the heme oxygenases led to the hypothesis that the CO system may play other roles than maintaining heme homeostasis and indicate that CO may function as an important biological molecule in a second-messenger capacity. Indeed, CO has been shown to activate guanylyl cyclase by displacing the iron out of the plane of the porphoryrin ring of the heme protein. The formed cGMP then activates cGMP-dependent kinases. Recent studies now show that HO-derived carbon monoxide plays a physiological role in the regulation of local vascular smooth muscle tone and platelet function through activation of soluble guanylyl cyclase.

Hence, dysregulation of the CO system may play an eminent role in the pathogenesis of the vascular proliferative disorders, like atherosclerosis and restenosis. Smooth muscle cell proliferation and migration into the vascular lesion play a key role in the pathogenesis of these occlusive vascular proliferative disorders, which form the major delimiter to the long term success rate of percutaneous (coronary) transluminal procedures as well as of arterial and venous bypass grafting.

The physical and thrombotic events accompanying PTCA and CABG procedures result in a cascade of mitogen, chemotactic factor and inflammatory cytokine release which all promote local vascular smooth muscle cell and immune competent cell recruitment, and reentering and progression through the cell cycle. Activated medial smooth muscle cells proliferate and migrate in the damaged intima and synthesize extracellular matrix, including fibrin and collagen, leading to the (re)occlusion of the vessel. Pharmacological interventions to avert this process of aberrant vascular cell proliferation and migration has been largely unrewarding.

Thus, there exists a need for safe, effective methods of inhibiting vascular smooth muscle cell proliferation and migration into the lumen of the blood vessel following injury to the blood vessel.

BRIEF SUMMARY OF THE INVENTION

The present invention provides a method for inhibiting vascular smooth muscle cell proliferation after balloon injury of a blood vessel in a mammal.

The present inventors have discovered that the CO generating system plays an important role in vascular injury and reactive vasospasm. Restoration of HO1 expression, and hence CO production, restores the loss of constitutively expressed endothelium-derived inhibitory factors that control local vascular tone, cell proliferation and migration, and platelet and immune cell adhesion resulting in inhibition of vascular lesion formation and normalized vasoreactivity.

The present invention provides a method comprising administering to a mammal in need thereof an expression constructs containing a nucleic acid encoding human heme oxygenase I. In another embodiment, the present invention encompasses methods for transforming cells in vivo using a nucleic acid encoding HO1 in an expression construct.

The present invention also encompasses expression constructs that comprise a promoter functional in eukaryotic cells and a nucleic acid encoding HO1, the nucleic acid being under transcriptional control of the promoter.

In a preferred embodiment, the expression constructs further comprise a polyadenylation signal. In another embodiment, the constructs further comprise a selectable marker. In a further embodiment, the expression construct is an adenovirus. In a preferred embodiment, the expression construct is an adenovirus that lacks at least a portion of the E1 region.

In certain embodiments, the nucleic acid is a cDNA. In other embodiments the nucleic acid is a genomic DNA. Still other embodiments include a combination of cDNA and genomic DNA, for example, in a mini-gene construct. In an exemplary embodiment the nucleic acid is positioned in a sense orientation with respect to said promoter.

The present invention also includes pharmaceutical compositions comprising an expression construct with a promoter functional in eukaryotic cells and a nucleic acid encoding HO1, along with a pharmaceutically acceptable buffer, solvent or diluent. In certain embodiments, the expression construct and pharmaceutically acceptable buffer, solvent or diluent are supplied in a kit.

The invention also provides a method for restoring proper HO1 function in a cell that either lacks HO1 function or has improper HO1 function. This method comprises transforming such a cell with an expression construct as described above, wherein the nucleic acid is positioned in a sense orientation. In a further embodiment, the cell is a cell of the blood vessel wall and, in still a further embodiment, the expression construct is an adenovirus.

Another embodiment of the invention is a method of treating a mammal with increased smooth muscle cell proliferation. This method comprises administering to an animal a pharmaceutical composition comprising an expression construct having a promoter functional in eukaryotic cells and a nucleic acid encoding HO1 in a pharmaceutically acceptable buffer, solvent or diluent.

DETAILED DESCRIPTION OF THE INVENTION

The present invention provides a method for inhibiting vascular smooth muscle cell proliferation after balloon injury of a blood vessel in a mammal, comprising introducing a DNA sequence to said blood vessel by catheter instillation at the site of said balloon injury after said balloon injury, said DNA sequence comprising a heme oxygenase I gene; and expressing said heme oxygenase I gene to produce heme oxygenase I protein in smooth muscle cells of said blood vessel, whereby said proliferating cells are killed.

The data presented here are the first to show that HO1 suppresses cell proliferation in vivo. Thus, the present invention addresses the need for improved therapy for restenosis and other diseases associated with increased cell proliferation. In particular, an expression construct capable of expressing a functional HO1 product can be used to inhibit cell proliferation.

There also is evidence that HO1-targeted treatments will have therapeutic implications in an anti-angiogenic approach. There are many disease where a decrease in vasculature is desirable. In addition, HO1-treatments also may prove beneficial with respect to other hyperproliferative disorders such as cancer.

Abbreviations

The following abbreviations are used herein:

| | |
|---|---|
| vsmc | vascular smooth muscle cell |
| HO1 | heme oxygenase 1 |
| Ad | Adenovirus |
| Ad-ntLacZ | recombinant adenovirus encoding for nuclear-tagged β-galactosidase |
| ΔE1A-Ad | sham adenovirus carrying a deletion of the E1A and E3 region |
| EC | endothelial cell |
| PDGF | platelet derived growth factor |
| FCS | fetal calf serum |
| BSA | bovine serum albumin |
| NOS | nitric oxide synthetase |
| NO° | nitric oxide |

HO1 and HO1-Related Nucleic Acids

The amino acid and nucleotide sequences encoding HO1 are known in the art (see Shibahara S, et al., "Cloning and expression of cDNA for rat heme oxygenase," Proc Natl Acad Sci U S A. 1985 Dec, 82(23):7865–7869; Yoshida et al., "Human heme oxygenase cDNA and induction of its mRNA by hemin.," Eur. J. Biochem. 1988 Feb. 1, 171(3):457–461).

The nucleic acid according to the present invention may encode an entire HO1 gene, a functional HO1 protein domain, or any HO1 polypeptide, peptide or fragment that is sufficient to effect inhibition of cell proliferation. The HO1 nucleic acid may be derived from genomic DNA, i.e., cloned directly from the genome of a particular organism. In preferred embodiments, however, the nucleic acid encoding HO1 would comprise complementary DNA (cDNA) or cDNA plus an intron, i.e., a mini-gene.

The term "cDNA" is intended to refer to DNA prepared using messenger RNA (mRNA) as template. The advantage of using a cDNA, as opposed to genomic DNA or DNA polymerized from a genomic, non- or partially-processed RNA template, is that the cDNA contains primarily the coding region of the corresponding protein and lacks nitrons and other non-coding regions found in genomic DNA.

Throughout the application, the term "HO1" is used to primarily refer to human heme oxygenase I, although other HO1 homologues from other species can also be used to practice the invention.

It also is contemplated that a given HO1 may be represented by natural variants that have slightly different primary sequences but, nonetheless, are biological functional equivalents of each other (see below). In order to function according to the present invention, all that is required is that the HO1 suppress cell proliferation. To test for such an affect, it is a simple matter to assay cell cycle progression analysis by flow cytometry and [$^3$H]thymidine incorporation, as described below in the example section.

As used in this application, the term "nucleic acid encoding a HO1" refers to a nucleic acid molecule that has been isolated free of total cellular nucleic acid. In preferred embodiments, the invention concerns a nucleic acid sequence essentially as set forth in SEQ ID NO:1; that is that the nucleic acid sequence substantially corresponds to a portion of SEQ ID NO:1 and has relatively few codons that are not identical, or functionally equivalent, to the codons of SEQ ID NO:1. The term "functionally equivalent codons" is used herein to refer codons that either encode the same amino acid (due to the degeneracy of the genetic code) or encode biologically equivalent amino acids.

Allowing for the degeneracy of the genetic code, sequences that have between about 50% and about 75%; or more preferably, between about 76% and about 99% of nucleotides that are identical to the nucleotides of SEQ ID NO:1 will be sequences that are "as set forth in SEQ ID NO:1." Sequences that are essentially the same as those set forth in SEQ ID NO:1 may also be functionally defined as sequences that are capable of hybridizing to a nucleic acid segment containing the complement of SEQ ID NO:1 under standard hybridization conditions. Suitable hybridization conditions will be well known to those of skill in the art. For example, a medium stringency condition could be provided by about 0.1 to 0.25M NaCl at temperatures of about 37° C. to about 55° C.

Naturally, the present invention also encompasses DNA segments that are complementary, or essentially complementary, to the sequence set forth in SEQ ID NO:1. Nucleic acid sequences that are "complementary" are those that are capable of base-pairing according to the standard Watson-Crick complementary rules. As used herein, the term "complementary sequences" means nucleic acid sequences that are substantially complementary, as may be assessed by the same nucleotide comparison set forth above, or as defined as being capable of hybridizing to the nucleic acid segment of SEQ ID NO:1 under relatively stringent conditions such as those described herein. Such sequences may encode the entire HO1 molecule or functional fragments thereof.

The DNA segments of the present invention include those encoding biologically functional equivalent HO1 proteins and peptides. Such sequences may arise as a consequence of codon redundancy and functional equivalency that are known to occur naturally within nucleic acid sequences and the proteins thus encoded. Alternatively, functionally equivalent proteins or peptides may be created via the application of recombinant DNA technology, in which changes in the protein structure may be engineered, based on considerations of the properties of the amino acids being exchanged. Changes designed by man may be introduced through the application of site-directed mutagenesis techniques or may be introduced randomly and screened later for the desired function.

If desired, one also may prepare fusion proteins and peptides, e.g., where the HO1 coding regions are fused with coding regions for other proteins or peptides and having desired functions, such as for purification, immunodetection, stabilization or targeting purposes. Furthermore, these fusion proteins or fusion peptides might contain an intracellular targeting sequence that would direct their transport to selected cellular compartments, particularly the nucleus. These fusion proteins or fusion peptides may be expressed from a DNA construct that has been delivered to animal cells.

It also will be understood that amino acid and nucleic acid sequences may include additional residues, such as additional N- or C-terminal amino acids or 5' or 3' sequences, and yet still be essentially as set forth in one of the sequences disclosed herein, so long as the sequence meets the criteria set forth above, including the maintenance of biological protein activity where protein expression is concerned. The addition of terminal sequences particularly applies to coding nucleic acid sequences that may, for example, include various non-coding sequences flanking either of the 5' or 3' portions of the coding region, such as promoters.

As mentioned above, modification and changes may be made in the primary structure of HO1 and still obtain a molecule having like or otherwise desirable characteristics. For example, certain amino acids may be substituted for other amino acids in a protein structure without appreciable loss of interactive binding capacity with structures such as, for example, antigen-binding regions of antibodies or binding sites on substrate molecules, receptors, or signal transduction. Since it is the interactive capacity and nature of a protein that defines that protein's biological functional activity, certain amino acid sequence substitutions can be made in a protein sequence (or, of course, its underlying DNA coding sequence) and nevertheless obtain a protein with like (agonistic) properties. Equally, the same considerations may be employed to create a protein or polypeptide with countervailing (e.g., antagonistic) properties. It is thus contemplated by the inventors that various changes may be made in the sequence of HO1 proteins or peptides (or underlying DNA) without appreciable loss of their biological utility or activity.

It also is well understood by the skilled artisan that, inherent in the definition of a biologically functional equivalent protein or peptide, is the concept that there is a limit to the number of changes that may be made within a defined portion of the molecule and still result in a molecule with an acceptable level of equivalent biological activity. Biologically functional equivalent peptides are thus defined herein as those peptides in which certain, not most or all, of the amino acids may be substituted. In particular, where the N-terminus of the HO1 protein is concerned, it is contemplated that only about 10 or more preferably, about 5 amino acids may be changed within a given peptide. Of course, a plurality of distinct proteins/peptides with different substitutions may easily be made and used in accordance with the invention.

Amino acid substitutions are generally based on the relative similarity of the amino acid side-chain substituents, for example, their hydrophobicity, hydrophilicity, charge, size, and the like. An analysis of the size, shape and type of the amino acid side-chain substituents reveals that arginine, lysine and histidine are all positively charged residues; that alanine, glycine and serine are all a similar size; and that phenylalanine, tryptophan and tyrosine all have a generally similar shape. Therefore, based upon these considerations, arginine, lysine and histidine; alanine, glycine and serine; and phenylalanine, tryptophan and tyrosine; are defined herein as biologically functional equivalents.

In making changes, the hydropathic index of amino acids may be considered. The importance of the hydropathic amino acid index in conferring interactive biological function on a protein is generally understood in the art (Kyte and Doolittle, "A simple method for displaying the hydropathic character of a protein," *J. Mol. Biol.*, 1982, 157(1):105–132). It is known that certain amino acids may be substituted for other amino acids having a similar hydropathic index or score and still retain a similar biological activity. In making changes based upon the hydropathic index, the substitution of amino acids whose hydropathic indices are within ±2 is preferred, those which are within ±1 are particularly preferred, and those within ±0.5 are even more particularly preferred.

It is understood that an amino acid can be substituted for another having a similar hydrophilicity value and still obtain a biologically equivalent protein. Hydrophilicity values have been assigned to the naturally encoded amino acid residues as detailed in U.S. Pat. No. 4,554,101. In making changes based upon similar hydrophilicity values, the substitution of amino acids whose hydrophilicity values are within ±2 is preferred, those which are within ±1 are particularly preferred, and those within ±0.5 are even more particularly preferred.

Expression Constructs

Throughout this application, the term "expression construct" is meant to include any type of genetic construct containing a nucleic acid coding for a gene product in which part or all of the nucleic acid encoding sequence is capable of being transcribed and translated into a protein.

In preferred embodiments, the nucleic acid encoding a HO1-derived product is under transcriptional control of a promoter. A "promoter" refers to a DNA sequence recognized by the synthetic machinery of the cell, or introduced synthetic machinery, required to initiate the specific transcription of a gene. The phrase "under transcriptional control" means that the promoter is in the correct location and orientation in relation to the nucleic acid to control RNA polymerase initiation and expression of the gene.

The term promoter will be used here to refer to a group of transcriptional control modules that are clustered around the initiation site for RNA polymerase 11. Suitable promoters are composed of approximately 7–20 bp of DNA, and containing one or more recognition sites for transcriptional activator or repressor proteins.

At least one module in each promoter functions to position the start site for RNA synthesis. The best known example of this is the TATA box, but in some promoters lacking a TATA box, such as the promoter for the mammalian terminal deoxynucleotidyl transferase gene and the promoter for the SV40 late genes, a discrete element overlying the start site itself helps to fix the place of initiation. Additional promoter elements regulate the frequency of transcriptional initiation. Typically, these are located in the region 30–110 bp upstream of the start site, although a number of promoters have recently been shown to contain functional elements downstream of the start site as well. The spacing between promoter elements frequently is flexible, so that promoter function is preserved when elements are inverted or moved relative to one another. In the tk promoter, the spacing between promoter elements can be increased to 50 bp apart before activity begins to decline. Depending on the promoter, it appears that individual elements can function either co-operatively or independently to activate transcription.

The particular promoter that is employed to control the expression of a nucleic acid encoding a HO1 is not believed to be important, so long as it is capable of expressing the nucleic acid in the targeted cell. Thus, where a human cell is targeted, it is preferable to position the nucleic acid coding region adjacent to and under the control of a promoter that is capable of being expressed in a human cell. Generally speaking, such a promoter might include either a human or viral promoter.

In various embodiments, the human cytomegalovirus (CMV) immediate early gene promoter, the SV40 early promoter and the Rous sarcoma virus long terminal repeat can be used to obtain high-level expression of HO1. The use of other viral or mammalian cellular or bacterial phage promoters which are well-known in the art to achieve expression of a HO1 is contemplated as well, provided that the levels of expression are sufficient for a given purpose.

By employing a promoter with well-known properties, the level and pattern of expression of a HO1 following transfection can be optimized. For example, selection of a promoter that is regulated in response to specific physiologic signals can permit inducible expression of HO1. Enhancers were originally detected as genetic elements that increased transcription from a promoter located at a distant position on the same molecule of DNA. This ability to act over a large distance had little precedent in classic studies of prokaryotic transcriptional regulation. Subsequent work showed that regions of DNA with enhancer activity are organized much like promoters. That is, they are composed of many individual elements, each of which binds to one or more transcriptional proteins. The basic distinction between enhancers and promoters is operational. An enhancer region as a whole must be able to stimulate transcription at a distance; this need not be true of a promoter region or its component elements. On the other hand, a promoter must have one or more elements that direct initiation of RNA synthesis at a particular site and in a particular orientation, whereas enhancers lack these specificities. Promoters and enhancers are often overlapping and contiguous, often seeming to have a very similar modular organization.

Any promoter/enhancer combination (as per the Eukaryotic Promoter Data Base EPDB) can be used to drive expression of a HO1. Use of a T3, T7 or SP6 cytoplasmic expression system is another possible embodiment. Eukaryotic cells can support cytoplasmic transcription from certain bacterial or viral promoters if the appropriate bacterial or viral polymerase is provided, either as part of the delivery complex or as an additional genetic expression construct.

Where a cDNA insert is employed, one will typically desire to include a polyadenylation signal to effect proper polyadenylation of the HO1 transcript. The nature of the polyadenylation signal is not believed to be crucial to the successful practice of the invention, and any such sequence may be employed. Also contemplated as an element of the expression cassette is a terminator. These elements can serve to enhance message levels and to minimize read through from the cassette into other sequences.

In preferred embodiments of the invention, the expression construct comprises a virus or engineered construct derived from a viral genome. The ability of certain viruses to enter cells via receptor-mediated endocytosis and to integrate into host cell genome and express viral genes stably and efficiently have made them attractive candidates for the transfer of foreign genes into mammalian cells.

The retroviruses are a group of single-stranded RNA viruses characterized by an ability to convert their RNA to double-stranded DNA in infected cells by a process of reverse-transcription. The resulting DNA then stably integrates into cellular chromosomes as a provirus and directs synthesis of viral proteins. The integration results in the retention of the viral gene sequences in the recipient cell and its descendants. The retroviral genome contains three genes, gag, pol, and env that code for capsial proteins, polymerase enzyme, and envelope components, respectively. A sequence typically found upstream from the gag gene, termed ψ, functions as a signal for packaging of the genome into virions. Two long terminal repeat (LTR) sequences are present at the 5' and 3' ends of the provirus. These contain strong promoter and enhancer sequences and are also required for integration in the host cell genome (Coffin, "Retroviridae and their replication," In: Fields B N, Knipe D M, ed. Virology. New York: Raven Press, 1990, pp.1437–1500).

In order to construct a retroviral vector, a nucleic acid encoding a HO1 is inserted into the viral genome in the place of certain viral sequences to produce a virus that is replication-defective. In order to produce virions, a packaging cell line containing the gag, pol, and env genes but without the LTR and ψ components is constructed. When a recombinant plasmid containing a human cDNA, together with the retroviral LTR and ψ sequences is introduced into this cell line (by calcium phosphate precipitation for example), the ψ sequence allows the RNA transcript of the recombinant plasmid to be packaged into viral particles, which are then secreted into the culture media. The media containing the recombinant retroviruses is then collected, optionally concentrated, and used for gene transfer. Retroviral vectors are able to infect a broad variety of cell types. Integration and stable expression require the division of host cells. However, evidence suggests that some of the viruses, including HIV and lentivirus, are capable of integrating and expressing in quiescent cells.

In vivo transformation of cells with retrovirus vectors show a limited ability to produce retroviral vector titers greater than $10^6$ infectious U/mL. Although titers of 10- to 1,000-fold higher are more desirable for in vivo applications, transformation with retroviral vectors is still possible.

Knowledge of the genetic organization of adenovirus, a 36 kB, linear and double-stranded DNA virus, allows substitution of a large piece of adenoviral DNA with foreign sequences up to 7 kB (Grunhaus and Horwitz, "Adenovirus as cloning vector," *Seminar in Virology*, 3:237–252, 1992). In contrast to retrovirus, the infection of adenoviral DNA into host cells does not result in chromosomal integration because adenoviral DNA can replicate in an episomal manner without potential genotoxicity. Also, adenoviruses are structurally stable, and no genome rearrangement has been detected after extensive amplification. Adenovirus can infect virtually all epithelial cells regardless of their cell cycle stage.

Adenovirus is particularly suitable for use as a gene transfer vector because of its mid-sized genome, ease of manipulation, high titer, wide target-cell range, and high infectivity. Both ends of the viral genome contain 100—200 base pair (bp) inverted terminal repeats (ITR), which are cis elements necessary for viral DNA replication and packaging. The early (E) and late (L) regions of the genome contain different transcription units that are divided by the onset of viral DNA replication. The E1 region (E1A and E1B) encodes proteins responsible for the regulation of transcription of the viral genome and a few cellular genes. The expression of the E2 region (E2A and E2B) results in the synthesis of the proteins for viral DNA replication. These proteins are involved in DNA replication, late gene expression, and host cell shut off. The products of the late genes, including the majority of the viral capsid proteins, are expressed only after significant processing of a single primary transcript issued by the major late promoter (MLP). The MLP (located at 16.8 m.u.) is particularly efficient during the late phase of infection, and all the mRNAs issued from this promoter possess a 5' tripartite leader (TL) sequence which makes them preferred mRNAs for translation.

In the current system, recombinant adenovirus is generated from homologous recombination between shuttle vector and provirus vector. Due to the possible recombination between two proviral vectors, wild-type adenovirus may be generated from this process. Therefore, it is critical to isolate a single clone of virus from an individual plaque and examine its genomic structure. Use of the YAC system is an alternative approach for the production of recombinant adenovirus.

Generation and propagation of the current adenovirus vectors, which are replication deficient, depend on a unique helper cell line, designated 293, which was transformed from human embryonic kidney cells by Ad5 DNA fragments and constitutively expresses E1 proteins (Graham et al., "Characteristics of a human cell line transformed by DNA from human adenovirus type 5", *J. Gen. Virol.*, 1977, 36:59–72). Since the E3 region is dispensable from the adenovirus genome, the current adenovirus vectors, with the help of 293 cells, carry foreign DNA in either the E1, the E3 or both regions (Graham and Prevec, "Manipulation of adenovirus vector," In: E. J. Murray (ed.), Methods in Molecular Biology: Gene Transfer and Expression Protocol, Clifton, N. J.: Humana Press, 1991, 7:109–128).

Helper cell lines may be derived from human cells such as human embryonic kidney cells, muscle cells, hematopoietic cells or other human embryonic mesenchymal or epithelial cells. Alternatively, the helper cells may be derived from the cells of other mammalian species that are permissive for human adenovirus. Such cells include, e.g., Vero cells or other monkey embryonic mesenchymal or epithelial cells. As stated above, the preferred helper cell line is 293.

Other than the requirement that the adenovirus vector be replication defective, or at least conditionally defective, the nature of the adenovirus vector is not believed to be crucial to the successful practice of the invention. The adenovirus may be of any of the 42 different known serotypes or subgroups A–F. Adenovirus type 5 of subgroup C is the preferred starting material in order to obtain the conditional replication-defective adenovirus vector for use in the method of the present invention. This is because Adenovirus type 5 is a human adenovirus about which a great deal of biochemical and genetic information is known, and it has historically been used for most constructions employing adenovirus as a vector.

As stated above, the typical vector according to the present invention is replication defective and will not have an adenovirus E1 region. Thus, it will be most convenient to introduce the nucleic acid encoding HO1 at the position from which the E1 coding sequences have been removed. However, the position of insertion of the HO1 coding region within the adenovirus sequences is not critical to the present invention. The nucleic acid encoding a HO1 transcription unit also may be inserted in lieu of the deleted E3 region or in the E4 region where a helper cell line or helper virus complements the E4 defect.

Adenovirus is easy to grow and manipulate and exhibits broad host range in vitro and in vivo. This group of viruses can be obtained in high titers, e.g., $10^9$–$10^{11}$ plaque-forming unit (PFU)/ml, and they are highly infective. The life cycle of adenovirus does not require integration into the host cell genome. The foreign genes delivered by adenovirus vectors are episomal, and therefore, have low genotoxicity to host cells. No side effects have been reported in studies of vaccination with wild-type adenovirus, demonstrating their safety and therapeutic potential as in vivo gene transfer vectors.

Adenovirus vectors have been used in eukaryotic gene expression (Levrero et al., "Defective and nondefective adenovirus vectors for expressing foreign genes in vitro and in vivo," *Gene* 1991,101:195–202; Gomez-Foix et al., "Adenovirus-mediated transfer of the muscle glycogen phosphorylase gene into hepatocytes confers altered regulation of glycogen," *J. Biol. Chem.* 1992, 267:25129–25134). Recently, animal studies suggested that recombinant adenovirus could be used for gene therapy (Stratford-Perricaudet and Perricaudet, "Gene transfer into animals: the promise of adenovirus," p. 51–61, In: *Human Gene Transfer*, Eds, O. Cohen-Haguenauer and M. Boiron, Editions John Libbey Eurotext, France, 1991; Stratford-Perricaudet et al., "Evaluation of the transfer and expression in mice of an enzyme-encoding gene using a human adenovirus vector," *Hum. Gene Ther*, 1990., 1:241–256; Rich et al., "Development and analysis of recombinant adenoviruses for gene therapy of cystic fibrosis," *Hum. Gene Ther.*, 1993, 4:461–476).

Other viral vectors may be employed as expression constructs in the present invention. Vectors derived from viruses such as vaccinia virus (Ridgeway, "Mammalian expression vectors," In: Rodriguez R L, Denhardt D T, ed. Vectors: A survey of molecular cloning vectors and their uses. Stoneham: Butterworth, pp. 467–492, 1988; Baichwal and Sugden, "Vectors for gene transfer derived from animal DNA viruses: Transient and stable expression of transferred genes," In: Kucherlapati R, ed. Gene transfer. New York: Plenum Press, pp.117–148,1986; Coupar et al., "A general method for the construction of recombinant vaccinia virus expressing multiple foreign genes," *Gene*, 68:1–10,1988) adeno-associated virus (AAV) (Ridgeway, 1988; Baichwal and Sugden, 1986; Hermonat and Muzycska, "Use of adenoassociated virus as a mammalian DNA cloning vector: Transduction of neomycin resistance into mammalian tissue culture cells," *Proc. Nat. Acad. Sci. USA*, 1984, 81:6466–6470) and herpesviruses may be employed. They offer several attractive features for various mammalian cells (Ridgeway, 1988; Baichwal and Sugden, 1986; Coupar et al., 1988; Horwich et al., "Synthesis of hepadinavirus particles that contain replication-defective duck hepatitis B virus genomes in cultured HuH7 cells," *J. Virol.*, 1990, 64:642–650.; Friedmann, "Progress toward human gene therapy," *Science*, 1989, 244:1275–1281). Replication-defective vectors derived from papillomavirus, parvovirus, lentivirus, etc. may also be used.

Methods for Gene Transfer

In order to effect expression of HO1 constructs, the expression construct must be delivered into a cell. This delivery may be accomplished in vitro, as in laboratory procedures for transforming cells lines, or in vivo or ex vivo, as in the treatment of certain disease states. The preferred mechanism for delivery is via in vivo delivery of a viral vector, preferably an adenoviral vector.

Viral Vectors

The delivery and entry of recombinant material into target cells is facilitated by use of vectors. DNA can be directly transferred to somatic target cells by viral vectors, such as retroviruses and adenoviruses, and non-viral methods, such as cationic liposomes, liposome viral conjugates, and polymers.

Viruses naturally infect mammalian cells and introduce their viral DNA to convert the host biosynthetic pathway to produce viral DNA, RNA, and protein. Molecular biologists have been able to modify these viruses so that they deliver foreign DNA to the target cell but cannot replicate in the host cell nor express viral proteins necessary for encapsulation. In general, early response viral sequences, involved in viral transcription, translocation or capsid synthesis, have been removed from the viral genome and are replaced by the foreign gene of interest.

Therefore, these recombinant viruses can only propagate in specific packaging cell lines which express the deleted viral proteins. Replication-deficient retroviruses, adenoviruses, adeno-associated viruses and adenoviral conjugates are now used in gene transfer techniques.

Retroviruses are RNA viruses that require vector integration into the host genome for expression of the transgene thus limiting their use to dividing cells. As most of the vascular and myocardial cellular components are non-replicating cells, retroviruses are of limited use in cardiovascular gene transfer. In addition, integration at random locations may lead to insertional mutagenesis and transformation. However, there have been no reported short- or long-term toxicity associated with their use in human gene therapy trials. Retrovirus-mediated gene transfer has been used for cell-mediated gene transfer using endothelial cells and for direct gene transfer into porcine arteries. The long-term, high-level expression renders retroviral vectors in particular ideal for ex vivo, cell-mediated gene transfer.

In cell-mediated gene transfer, endothelial cells or vascular smooth muscle cells may be isolated, expanded and transduced in the laboratory and reseeded on to an artery in vivo. The technique of ex vivo gene transfer is however fairly cumbersome since it requires cell expansion. However, ex vivo gene transfer of endothelial cells and smooth muscle cells may be useful in seeding stents, grafts or injured arteries during vascular procedures to treat thrombotic disorders or graft hyperplasia.

Recombinant gutted lentiviruses may represent an attractive alternative to retroviruses. Lentiviruses have not been directly implicated in any malignancies and, in contrast to retroviral based vector systems, human, simian and bovine immunodeficiency viral (HIV, BIV, SIV) vector systems have been shown to mediate stable gene transfer in terminally differentiated neurons and macrophages in culture. In vivo, transgene expression is detected for up to 6 months in liver, muscle, retinal tissue, and brain of immune-competent rats in vivo and does not appear to evoke an immune response or local inflammation, permitting repeated viral challenge.

Recombinant adenoviruses efficiently transfect proliferating and non-proliferating cells, but lack mutagenicity since the transgenic genome is not integrated into the host chromosome but remains episomal. Deletions of EI A, EI B, E2 and E3 regions of the viral genome prevent viral replication in transfected cells, reduce expression of early response viral proteins, and hence, limit cellular inflammation. Recombinant adenoviruses have been successfully used for in vivo gene transfer in carotid and jugular veins rat and rabbit myocardium and rabbit peripheral arteries. In vivo adenovirus-mediated gene transfer using biological active gene products have also been shown to exert effects in vascular diseases. Since immunogenicity remains limiting in adenoviral vectors, adenoviral vectors gutted of almost the entire adenoviral genome may prove to be beneficial in circumventing the deleterious immune response.

Recombinant adeno-associated viruses (rAAV) are promising vectors given the ability to integrate into the host genome, resulting in stable transgenic expression, and lack of immunogenicity due to a lack of viral genes in the vector that express surface proteins. rAAV vectors are described in U.S. Pat. No. 5,139,941. rMV has not been associated with disease in any host and has not been associated with malignancies despite integration of the transgene into the host genome. rAAV integrates viral and transgenic DNA preferentially but not exclusively at chromosome 19q locus. Adeno-associated viruses are incapable of replication and depend on co-infection with adenovirus or a herpesvirus for replication. In vivo, long-term expression of p-galactosidase and tyrosine hydroxylase have been achieved in non-dividing neurons in the rat CNS by rAAV, and intravenous delivery of rAAV encoding human clotting factor IX resulted intransduction of 3% of all hepatocytes over a 5 month observation period. Also, intraluminal and periadventitial vascular delivery of rAAV in atherosclerotic carotid arteries of cynomolgus monkeys results in efficient transgenic expression. However, in contrast to retroviruses and adenoviruses, transgenic expression is predominantly found in adventitial endothelial cells of microvessels.

Other viral vectors that may be used for gene therapy include herpes simplex virus (U.S. Pat. No. 5,288,641) and cytomegalovirus (Miller, 1992).

Non-viral Vectors

Because of safety concerns regarding viral vectors, an interest arose in developing synthetic delivery system avoiding the infectious complications presented by the first generation viral vectors. Non-viral gene transfer can be performed by microinjection, DEAE-dextran transfection, calcium phosphate precipitation, electroporation, liposomes, and particle-mediated gene transfer (i.e. introducing DNA-coated particles).

The most common non-viral gene transfer vectors are DNA-liposomes. Cationic liposomes condense and entrap the DNA through electrostatic interaction. They are prepared by sonification and remain stable in aqueous solution for months. The positively charged liposome complex fuses with the negatively charged cell surface to release the DNA into the cytoplasm of target cells, bypassing the lysosomal compartment and degradation by serum. It is postulated that plasmid DNA is subsequently incorporated in the nucleus as an episome. The relatively safe profile of liposomes, the lack of vector size or target cell constraints, as well as the relative ease of liposome-DNA complex preparation favors this gene transfer technique.

Preclinical studies using different forms of these lipids (DOTMA, DC-Chol, DMRIE, and DLRIE) have shown promise for efficient in vivo transfection. Lipofection-mediated gene transfer, using either catheter-based delivery or direct injection, results in site-specific expression of foreign recombinant genes in vascular endothelial and smooth muscle cells and alters the biology of the vessel wall. Cationic liposomes are well tolerated in vivo and do not induce any biochemical, hemodynamic or cardiac intoxications.

Additional advances in lipid chemistry are developing newer generations of cationic liposomes, which permit higher transfection with minimal toxicity. The transfection efficacy and specificity of lipofection may be further augmented by coupling of ligands or viral particles (Ad, HVJ, VSVG) to the liposomes. In particular, HVJ-coated liposomes have been successfully utilized to transduce venous bypass grafts ex vivo and in vivo.

In certain embodiments, plasmid DNA or RNA may be injected directly into tissue such as skeletal muscle or myocardium. In other embodiments, anti-sense oligonucleotides are used for gene therapy (Morishita et al., 1993). Anti-sense oligonucleotides do not require a vector for cell transduction and can be directly injected in the target tissue. Anti-sense oligonucleotides are short DNA sequences complementary to the RNA message of interest, which are chemically modified to resist nuclease degradation. The oligonucleotide may be modified at the 5; end to prevent nuclease degradation or may made up of ribonucleotide bases attached to a peptide backbone (protein nucleic acid).

Various animal and cell culture studies have shown that anti-sense oligonucleotides are able to efficiently modify intracellular expression of factors involved in smooth muscle cell and endothelial cell migration and proliferation, including by use of anti-sense oligonucleotides against c-myc, c-myb, cdc2, and PCNA. The nucleotide sequence hybridizes to target RNA, which prevents translation of RNA, targets the message for degradation by ribonuclease H, and interferes with cytosolic translocation.

GENE TRANSFER IN THE CARDIOVASCULAR SYSTEM

In certain embodiments of the present invention, gene therapy is used to treat or prevent cell proliferation. In preferred embodiments, vascular cell proliferation such as that associated with restenosis or atherosclerosis is prevented using gene therapy. It is contemplated that a gene therapy vector or composition of the present invention may be tested in an animal model. Studies in animal models of cardiovascular disease have demonstrated that transgenes can be expressed at high levels at local sites in the vasculature.

Local Delivery to the Vasculature

An attractive feature of cardiovascular gene transfer is that recombinant genes may be delivered to local sites in the vasculature by a medical device. Medical devices that are suitable for use in the present invention include known devices for the localized delivery of therapeutic agents. Such devices include, for example, catheters such as injection catheters, balloon catheters, double balloon catheters, microporous balloon catheters, channel balloon catheters, infusion catheters, perfusion catheters, etc., which are, for example, coated with the therapeutic agents or through which the agents are administered; needle injection devices such as hypodermic needles and needle injection catheters; needleless injection devices such as jet injectors; coated stents, bifurcated stents, vascular grafts, stent grafts, etc.; and coated vaso-occlusive devices such as wire coils.

Exemplary devices are described in U.S. Pat. Nos. 5,935, 114; 5,908,413; 5,792,105; 5,693,014; 5,674,192; 5,876, 445; 5,913,894; 5,868,719; 5,851,228; 5,843,089; 5,800, 519; 5,800,508; 5,800,391; 5,354,308; 5,755,722; 5,733, 303; 5,866,561; 5,857,998; 5,843,003; and 5,933,145; the entire contents of which are incorporated herein by reference. Exemplary stents that are commercially available and may be used in the present application include the RADIUS™ (Scimed Life Systems, Inc.), the SYMPHONY® (Boston Scientific Corporation), the WALLSTENT (Schneider Inc.), the Precedent II™ (Boston Scientific Corporation) and the NIR™ (Medinol Inc.). Such devices are delivered to and/or implanted at target locations within the body by known techniques.

The double balloon catheter was an initial catheter employed in animal model studies and was useful to demonstrate the basic principles of gene transfer. The catheter consists of two balloons placed about 1.5 cm apart with an inner protected space. The genetic vector is instilled into the isolated arterial segment between the balloons. Adenoviral-mediated recombinant gene expression is detected in endothelial cells, vascular smooth muscle cells and adventitial cells for several weeks following infection and is not found downstream to the arterial segment or in other tissues by PCR. Retroviral-mediated gene expression can be detected for up to 6 months. A disadvantage to this catheter is the possibility of distal ischemia due to occlusion of blood flow. Alternate delivery devices permit flow distal to the isolated segment allowing a prolonged instillation time period without compromising distal perfusion.

Porous and microporous balloons infuse the vector directly into the juxtapositioned arterial wall through small pores in the catheter. The depth of delivery is directly related to the perfusion pressure. Channel balloon catheters combine two separate inflatable compartments for balloon angioplasty and drug infusion, allowing separate control of balloon inflation pressure for positioning and drug infusion pressure. A hydrogel coated balloon catheter has a hydrophilic polyacrylic acid polymer coating of the balloon. This polymer absorbs the DNA suspension and when the balloon is inflated, the DNA coating is pressed against the vessel wall. The iontophoretic balloon uses a local current between the balloon and the skin of the subject to drive the negatively charged DNA into the arterial wall.

Other delivery devices include stents coated with a DNA-impregnated polymer or cells comprising a nucleic acid of the present invention (ex vivo gene transfer) into arterial and venous grafts. Furthermore, tissue may be selectively targeted for gene therapy by use of tissue specific promoters and enhancers.

Myocardial Delivery

In certain embodiments of the present invention, nucleic acid or protein compositions of the present invention may be introduced into the myocardium. Myocardial gene transfer requires tranfection of terminally differentiated myocytes. Adenoviral gene transfer by intracoronary or intramyocardial delivery results in transient gene expression for several weeks in a limited number of cells. Adeno-associated viral vectors have been shown to induce stable transgene expression in up to 50% of murine, rat and porcine cardiomyocytes after ex vivo intracoronary infusion and myocardial injections for at least 6 months. These vectors may be useful for gene delivery to treat human myocardial diseases.

Vascular Diseases

Many vascular diseases are characterized by abnormalities of cell proliferation. One approach to therapies is to express genes that inhibit cell proliferation within vascular lesions, for example, after angioplasty or in a by-pass graft. Most approaches regulate the cell cycle in vascular smooth muscle, endothelial or macrophage cells.

Progression through the cell cycle is regulated by the assembly and phosphorylation of cyclin/cyclin-dependent kinase complexes (CDKs). Endogenous inhibitors of the cyclin-CDKs, termed the cyclin-dependent kinase inhibitors (CKIs) result in cell cycle arrest and cessation of cell proliferation.

Genetic strategies to abrogate vascular lesion formation have focused on regulatory gene products that interfere with DNA synthesis, cell cycle progression, and cell viability. Gene products interfering with DNA and RNA replication have been evaluated for their capacity to block smooth muscle cell proliferation and reduce vascular lesion formation. Prodrug-enzyme therapies, using thymidine kinase or cytosine deaminase, constitute a form of local therapy in which an enzyme is expressed locally that converts a prodrug into an active form. Gene transfer of DNA encoding these converting enzymes to the injured arterial wall combined with systemic prodrugs administration produces high levels of growth inhibitory drugs in the target tissue. The therapeutic effect of transgene expression can be regulated by administration of the prodrug and can be initiated independently of the gene transfer.

Herpes simplex virus thymidine kinase (HSV-tk) converts an inert nucleoside analog, ganciclovir into a phosphorylated, toxic form in transduced cells. Its subsequent incorporation into the host DNA induces chain termination and cell death in dividing cells, while non-dividing cells remain unaffected. Local delivery of recombinant adenovirus encoding for HSV-tk at the time of the balloon injury and systemic administration to ganciclovir inhibited smooth muscle cell proliferation in vivo, and decreased intimal formation in balloon-injured porcine and rat arteries and atherosclerotic rabbit arteries. A similar reduction of neointimal hyperplasia was observed in arterial interposition grafts which overexpress HSV-tk in the rabbit. Cytosine deaminase (CD) catalyzes the hydrolytic deamination of non-toxic cytosine and 5-fluorocytosine (5-FC) into uracil and 5-fluorouracil, which inhibits thymidilate synthase and hence DNA and RNA synthesis. In human and rabbit primary smooth muscle cells, CD/5-FC does not induce significant necrosis or apoptosis but results in cytostatic effects on vascular smooth muscle cells. CD gene transfer in the rabbit femoral injury model followed by systemic 5-FC treatment resulted in a decrease of the intima to media area ratio, comparable to the efficacy of HSV-tk/ganciclovir in a rat and pig model of vascular injury.

The Fas/FasL death-signaling pathway mediates cellular immunocytotoxicity in activated lymphocytes. Binding of the Fas receptor to FasL activates the caspase pathway leading to apoptosis. FasL is expressed in intimal smooth muscle cells and immune competent cells in atherosclerotic plaques. Studies using adenoviral-mediated gene transfer of FasL to balloon-injured rat carotid arteries demonstrated an attenuation of T cell extravasation in FasL expressing arteries as opposed to sham virus treated arteries, accompanied with a 60% reduction of neointima formation (intima/media area ratio). FasL may function to protect the vessel from leukocyte extravasation to the subendothelial space during arterial repair by inducing T lymphocyte apoptosis.

Targeting of cell cycle regulatory proteins promotes inhibition of cell proliferation, and cell differentiation. Cell cycle arrest prevents vsmc proliferation and migration and endothelial dysfunction, shown by improved vasoreactivity and NO production, rendering the vessel less susceptible to inflammatory infiltration and free radical formation.

Progression through the cell cycle is controlled by the assembly and disassembly of the different cyclin-cyclin dependent kinase complexes. These complexes phosphorylate retinoblastoma protein leading to the release of the sequestered transcription factors, E2F and Elf 1. The cyclin dependent kinase inhibitors (CKIs) modulate the enzymatic activity of cyclin/CDK complexes necessary for $G_1$ progression. In vivo, Ad-p21 infection of porcine iliofemoral and rat carotid arteries following balloon injury reduces BrdU incorporation by 35% and I/M area ratio by 37%. Likewise, Gax homeobox gene overexpression, as an upstream regulator of p21, in the rat carotid artery injury model inhibited neointimal formation and luminal narrowing by 59 and 56 percent, respectively. Adenovirus-mediated overexpression of p27 in balloon-injured rat and porcine arteries significantly attenuated intimal lesion formation.

The effects of many cyclin-CDK and CKI interactions are mediated through their effect on the phosphorylation status and therefore activity of retinoblastoma gene product (Rb). Rb inhibits cell cycle progression from $G_1$ into S phase by sequestering and inactivating a set of cellular transcription factors. Localized infection of porcine endothelial cells and vsmc with Ad-ΔRb, an unphosphorylatable, constitutively active Rb, results in a significant reduction in cell proliferation and [$^3$H]thymidine incorporation, yet the cells remain viable. In the rat carotid artery injury as well as in the pig balloon injury model, ΔRb expression results in a 42–47% decrease in the neointima/media area ratio relative to control arteries.

Alternatively, inhibition of the cell cycle in human vein grafts with ex vivo treatment of E2F decoy oligodeoxynucleotide reduces not only graft susceptibility to atherosclerosis, and enhances medial hypertrophy, which renders the graft more resistant to increased hemodynamic stress and improves vein graft patency.

Metalloproteinases degrade the extracellular matrix, promote growth factor release and cell activation and are therefor essential for cell migration. Overexpression of tissue inhibitor of metalloproteinases (TIMP) was shown to inhibit invasive and metastatic behavior of tumor cells. The effects of TIMP protein expression has been evaluated in an organ culture model of neointimal formation, which lends itself for the study of smc migration rather than proliferation. Overexpression of TIMPi and 2 reduced neointima formation and neointimal cell numbers by 54–79% and 71% respectively, but did not alter smc proliferation and viability. These data confirm the importance of metalloproteinases and smc migration to the development of neointimal hyperplasia and suggest that a combined anti-proliferative and anti-migratory gene therapy approach may optimize lesion reduction.

Other methods aim to reconstitute endothelial derived inhibitory signals, which prevent leukocyte adhesion and platelet aggregation, relax local muscle tone and inhibit vsmc proliferation by gene transfer of iNOS or eNOS. The NOS pathway has been shown to play a significant role in a number of cardiovascular disorders including atherosclerosis, systemic and pulmonary hypertension, ischemia-reperfusion, hypercholesterolemia, and vasospasm. L-arginine feeding, iNOS and eNOS gene transfer and various NO donors have shown to successfully reduce lesion formation in hypercholesterolemic rabbits and neointimal hyperplasia following arterial balloon injury model in pigs and rats.

Thus, studies in various animal models demonstrate that genetic approaches are feasible and effective in limiting cell proliferation, migration and extracellular matrix deposition. The HO1 encoding nucleic acids may be particularly useful in methods of treating cardiovascular disease. For example, a nucleic acid encoding HO1 may be introduced locally into an injured artery to prevent restenosis.

In other embodiments, gene therapy using a nucleic acid of the present invention may be combined with other gene and non-gene therapies to treat a cardiovascular disease. Potential molecular targets for cardiovascular disease are shown in Table 5.

TABLE 5

Potential molecular targets for cardiovascular disease

| Pathophysiology | Molecular Target |
|---|---|
| Endothelial dysfunction & endothelial injury | NOS-NO donors VEGE; FGF, Fas-L |
| Abnormal smc proliferation | CKIs, E2F decoy, Rb mutants, TK/ganciclovir; CD/5-fluorocytosine; FasL |
| Thrombosis | Tissue factor inhibitors; anti-thrombin agents |
| Abnormal smc migration | Metalloproteinase inhibitors (TIMP); plasminogen activator inhibitors |
| Abnormal apoptosis | Bcl-2 inhibitors, Bax or CPP32 inducers |
| Plaque rupture | Metalloproteinase inhibitors; leukocyte adhesion blockers |
| Neoangiogenesis | a/bFGF; VEGF; Angiopoietin |
| Dyslipidemia | LDL-R, ApoE, ApoA, LPL |
| Systemic/Pulmonary Hypertension | NOS-NO donors |
| Graft failure | NOS - NO donors; TPA; FasL; E2F decoy; TGFβ |
| Heart failure | Bcl-2 inhibitors, Bax or CPP32 inducers MyoD; fetal myocyte transplant; $β_2$ adrenergic receptor/ $β_2$ adrenergic receptor kinase SR Ca(2+) pumps |

HO1 Expression Constructs in Combination With Other Therapies

The method of the present invention can be combined with other methods for treating cell proliferation. For example, other genes such as thymidine kinase, cytosine deaminase, p21, p27, and p53 and combinations thereof can be concomitantly transformed into cells and expressed. For example, the herpes simplex-thymidine kinase (HS-tK) gene, when delivered to blood vessel walls by a adenoviral vector system, successfully resulted in the decrease in neointimal proliferation associated with restenosis (Chang et al., Mol. Med., 1995, 172–181). In the context of the present invention, it is contemplated that HO1 gene expression could be used similarly in conjunction with other gene therapy approaches. The genes may be encoded on a single nucleic acid but separately transcribed. Alternatively, the genes may be operably linked such that they are contranscribed. In preferred embodiments, the genes are operably linked to encode a fusion protein. In other embodiments the co-transcribed genes are separated by an internal ribosome binding site allowing the proteins to be translated separately. Such combination therapies are described in WO 99/03508 (incorporated herein by reference in its entirety).

Pharmaceutical Compositions and Routes of Administration

Where clinical application of an expression construct comprising a nucleic acid encoding HO1 is contemplated, it will be necessary to prepare the complex as a pharmaceutical composition appropriate for the intended application. Generally this will entail preparing a pharmaceutical composition that is essentially free of pyrogens, as well as any other impurities that could be harmful to humans or animals. One also will generally desire to employ appropriate salts and buffers to render the complex stable and allow for complex uptake by target cells.

Aqueous compositions of the present invention comprise an effective amount of the expression construct and nucleic acid, dissolved or dispersed in a pharmaceutically acceptable carrier or aqueous medium. Such compositions can also be referred to as inocula. The phrases "pharmaceutically or pharmacologically acceptable" refer to molecular entities and compositions that do not produce an adverse, allergic or other untoward reaction when administered to an animal, or a human, as appropriate. As used herein, "pharmaceutically acceptable carrier" includes any and all solvents, dispersion media, coatings, antibacterial and antifungal agents, isotonic and absorption delaying agents and the like. The use of such media and agents for pharmaceutical active substances is well known in the art. Except insofar as any conventional media or agent is incompatible with the active ingredient, its use in the therapeutic compositions is contemplated. Supplementary active ingredients also can be incorporated into the compositions.

Solutions of the active compounds as free base or pharmacologically acceptable salts can be prepared in water suitably mixed with a surfactant, such as hydroxypropylcellulose. Dispersions also can be prepared in glycerol, liquid polyethylene glycols, and mixtures thereof and in oils. Under ordinary conditions of storage and use, these preparations contain a preservative to prevent the growth of microorganisms.

The expression constructs and delivery vehicles of the present invention may include classic pharmaceutical preparations. Administration of therapeutic compositions according to the present invention will be via any common route so long as the target tissue is available via that route. Preferably administration will be by intravenous injection or catheter delivery to the site of blood vessel injury. Such compositions would normally be administered as pharmaceutically acceptable compositions that include physiologically acceptable carriers, buffers or other excipients.

The therapeutic compositions of the present invention are advantageously administered in the form of injectable compositions either as liquid solutions or suspensions; solid forms suitable for solution in, or suspension in, liquid prior to injection may also be prepared. These preparations also may be emulsified. A typical composition for such purpose comprises a pharmaceutically acceptable carrier. Other pharmaceutically acceptable carriers include aqueous solutions, non-toxic excipients, including salts, preservatives, buffers and the like. Examples of non-aqueous solvents are propylene glycol, polyethylene glycol, vegetable oil and injectable organic esters such as ethyloleate. Aqueous carriers include water, alcoholic/aqueous solutions, saline solutions, parenteral vehicles such as sodium chloride, Ringer's dextrose, etc. Intravenous vehicles include fluid and nutrient replenishers. Preservatives include antimicrobial agents, anti-oxidants, chelating agents and inert gases. The pH and exact concentration of the various components the pharmaceutical composition are adjusted according to well known parameters.

Kits

All the essential materials and reagents required to practice the method of the present invention may be assembled together in a kit. This generally will comprise selected expression constructs. Also included may be various media for replication of the expression constructs and host cells for such replication. Such kits will comprise distinct containers for each individual reagent.

When the components of the kit are provided in one or more liquid solutions, the liquid solution preferably is an aqueous solution, with a sterile aqueous solution being particularly preferred. For in vivo use, the expression construct may be formulated into a pharmaceutically acceptable syringeable composition.

The components of the kit may also be provided in dried or lyophilized forms. When reagents or components are provided as a dried form, reconstitution generally is by the addition of a suitable solvent. It is envisioned that the solvent also may be provided in another container means.

The kits of the present invention also will typically include a means for containing the vials in close confinement for commercial sale such as, e.g., injection or blow-molded plastic containers into which the desired vials are retained.

Irrespective of the number or type of containers, the kits of the invention also may comprise, or be packaged with, an instrument for assisting with the injection/administration or placement of the ultimate complex composition within the body of an animal. Such an instrument may be an syringe, catheter or any such medically approved delivery vehicle or device.

The following examples are included to demonstrate preferred embodiments of the invention. It should be appreciated by those of skill in the art that the techniques disclosed in the examples which follow represent techniques discovered by the inventors to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

EXAMPLES

Recombinant HO1 Expression in Vascular Cell Culture

Replication-defective adenoviruses encoding human HO1 (Ad-HO1),nuclear-tagged β-galactosidase (Ad-ntLacZ) and E1A-deficient sham virus(ΔE1A-Ad) were constructed by homologous recombination in 293 cells. Expression of HO1 in the adenoviral vector was regulated by the CMV enhancer/promoter and bovine growth hormone polyadenylation sequence. Recombinant viral stocks containing less than 1 pfu wild type adenovirus per $1\times10^9$ pfu recombinant adenovirus were used throughout the procedures.

Recombinant HO1 expression was confirmed in primary aortic porcine vascular smooth muscle cells (vsmc), porcine endothelial cells(ec) and human renal carcinoma cells (293) by using western blot analysis. Significant protein levels could be detected in a dose-dependent manner, 48 hours after HO1 gene transfer. Sham ΔE1A-virus did not alter HO1 expression in vascular cells. Transfection efficiency in vsmc at moi 500 and 1000 was respectively 75% to 100%. 48 hours following infection as determined by parallel infection with recombinant adenovirus encoding for nuclear tagged LacZ. Steady-state cGMP levels were increased by 128% as compared to basal levels. Specific inhibition of HO1 by zinc(II)protoporphyrin IX (ZnPP IX) or inhibition of guanylate cyclase (by ODQ) normalized cGMP generation, whereas specific inhibitors of NOS(L-NAME) or cAMP (Rp-cAMPS) signaling pathways did not affect cGMP levels, indicating that HO1 affects cGMP by directly activating guanylate cyclase through CO production.

Deletion of the HO1 Locus Promotes Cell Proliferation and Progression in G1/S (ie., escape G1 cell cycle arrest).

To determine the effect of HO1 on cell proliferation under more physiological conditions, HO1 nullizygous primary vsmc were compared to vascular cell derived from wild type litter mates. Deletion of the HO1 locus facilitated/increased/ stimulated cell growth/mitogenesis and DNA synthesis. The cell number was enhanced by 80.2% ±11.7 72 hours following restimulation, whereas [$^3$H] incorporation was increased 3.1-fold. Flow cytometric analysis demonstrated that entry into the S/G2 phase was facilitated in the HO1 null vsmc compared to controls.

Endogenous HO1 Plays a Role in the Process of Arterial Remodeling after Injury

To determine the function of HO1 in the response to arterial injury and vascular cell proliferation, the HO1 expression pattern in vascular lesion formation was examined. The pig arterial balloon injury model is a well-established model of human vascular proliferative disease and of restenosis in particular. Porcine iliofemoral arteries were injured using a balloon catheter and subsequently infected with recombinant Ad-HO1or ΔE1A-Ad ($1\times10^{12}$ particles) using a double-balloon catheter as described previously (Nabel et al., Science, 249:1285–1288, 1990).

Typically, arterial injury will result in a vascular proliferative lesion within 2–3 weeks after surgery. With BrdU incorporation, vsmc proliferation can be detected in the vascular wall as early as 2 days after injury and is limited to the first 7 days of arterial response. Immunohistochemical analysis of quiescent porcine arteries showed that HO1 was consecutively expressed in medial vsmc and to a lesser degree in endothelial cells. Within 4 days after balloon injury, HO1 expression decreased while cell proliferation increased in intimal and medial vsmcs. Two weeks after injury, HO1 was highly expressed in intimal and medial vsmcs and correlated with a decline in cell proliferation (Tanner et al., Circ. Res., 1997) suggesting that HO1/CO functions as an endogenous inhibitor of vsmc growth. HO1 was expressed more predominantly adjacent to the internal elastic lamina.

The temporal and spatial expression pattern of HO1 after arterial injury in the pig concurs with the expression pattern of the cell cycle regulatory proteins, p21, p27, and p57 (Tanner et al., Circ. Res., 1997), suggesting that HO1/CO may play a role in the upstream transduction pathway leading to the expression of cyclin dependent kinase inhibitors and hence G1/G0 cell cycle arrest, exit and cell differentiation. Indeed, the lower regions of the neointima have also been associated by low vsmc mitogenesis and procollagen synthesis (Tanner et al., Circ. Res., 1997). Western blot analysis of arterial homogenates confirmed the immunohistological data. Although expression levels may vary between different animals, HO1 protein expression was lost directly after arterial injury and upregulated between day 7 and 21 post injury (pi) and correlated inversely to cell proliferation.

HO1 Overexpression Leads to cGMP-mediated G1 Cell Cycle Arrest and Long Term Growth Inhibition In Vascular Cells.

The effect of HO1 on cell proliferation and cell cycle progression was determined in vsmc and 3T3 cell lines infected with Ad-HO1 or sham virus. After 24 hours incubation, the cells were arrested in G1/G0 by mitogen deprivation for 24 hours and restimulated to proliferate again. No differences in cell viability were observed after viral infection and 24 hours serum deprivation between control (non infected or ΔE1A-Ad infected cells) and Ad-HO1 infected cultures as determined by trypan blue exclusion, numbers of non adherent cells after virus incubation, and ANNEXIN-V-FLUOS-aided flow cytometry cells after virus incubation.

In primary vsmc, HO1 encoding adenovirus infection, but not ΔE1A sham adenovirus, resulted in dose dependent inhibition of cell proliferation by 62.9%, 86% and 95.5% respectively at moi 250, 500 and 1000 at 72 hours following restimulation. $H^3$-thymidine incorporation was reduced by 95% in HO1 expressing cells. The effect on DNA synthesis could be reversed by HO1 inhibition (ZnPP IX), but not by NOS inhibition (L-NAME). Soluble guanylate cyclase (sGC) inhibition and competitive inhibition of cGMP (Rp-8-BrcGMPS) as well as cAMP (Rp-cAMPS), were also able to restore $H^3$-thymidine incorporation under HO overexpression, suggesting that HO1 attenuates cell proliferation through guanylate cyclase activation by CO production.

The generated cGMP may modulate cell proliferation by affecting the enzyme activity of cGMP-dependent kinases, as well as of cAMP-dependent kinases by shedding. HO1 did not inhibit proliferation due to metabolic cytostasis since protein synthesis was unaffected by adenoviral infection as measured by Bradford analysis. The growth inhibition was associated with an induction of p21 cyclin dependent kinase but did not upregulate p27 and p57 protein levels. Propidium iodide-aided flow cytometric analysis indicated that expression of HO1 resulted in a dose-dependent accumulation of cells in G1/G0 phase of the cell cycle, suggesting arrest predominantly at the G1/S transition. Similar observations were made in 3T3 fibroblast cell line.

Transgenic Expression in Porcine and Rat Iliofemoral Arteries Induces Vasorelaxation HO is expressed constitutively by vascular endothelial cells. It has been suggested that this basal release of CO can regulate local vascular tone and perfusion of several organ systems. Hence, dysregulation of CO and NO production (loss of production or inappropriate level) after arterial balloon injury or physical manipulation during bypass surgery may lead to unopposed arterial vasoconstriction and graft failure.

Here, the effects of in vivo transgenic HO1 expression on vascular constriction in isolated arterial rings was determined. Iliofemoral porcine arteries were infected with Ad-HO1 or ΔE1A-Ad and after 4 days, carefully collected and used for ex vivo vasoreactivity studies. To rule out a possible effect through a NOS dependent mechanism, all vasoreactivity studies were carried out in the presence of L-NNA to inhibit NO synthase.

Although the arteries were not intentionally injured during the gene transfer by wire or balloon, no endothelium-derived vasorelaxation could be elicited by acetylcholine stimulation in any of the arteries indicating endothelial dysfunction or denudation. HO1 expression resulted in a potent vasorelaxation in porcine vascular rings. Maximal isometric force under phenylephrine stimulation was reduced 5-fold in HO1 infected arteries (80%) as compared to sham-treated arteries. $EC_{50}$ in HO1 expressing vessels was increased by 0.5 log as compared to control arteries. Inhibition of HO1 by ZnPP IX restored the $EC_{50}$ to control levels, but could only partially restore maximal contractile force in transfected arteries (to 69.5% of control value).

HO1 Transgene Expression in Injured Arteries Significantly Reduces Neointima Formation due to Inhibition of Vascular Cell Proliferation To assess the effect of HO1 on vascular lesion development and vsmc proliferation in vivo, injured porcine arteries were co-infected with Ad-HO1or an ΔE1A-Ad control. Concomitant HO1 gene transfer inhibited neointimal hyperplasia formation by 75% at 1 week and 63% at 3 weeks post injury. Mean perimeters of the internal and the external elastic lamina did not differ between the experimental groups at 1 and 3 weeks. Histological analysis of the HE stained arteries did not show clear morphological changes beside the increase of luminal diameter due to the inhibition of vascular lesion development. DNA synthesis in vascular cells was significantly inhibited in HO transgenic arteries at 7 days after HO gene transfer, as compared to ΔE1A-Ad transfected arteries (t.media; 70% decrease; t.initima: 49% decrease). These observations further confirm our in vitro data and provide a molecular basis for the inhibition of intimal hyperplasia in vivo by HO1 overexpression.

Thus, early restoration of lost HO1/CO expression after arterial injury and endothelial dysfunction may reinstate the endothelium-derived growth and migratory inhibitory signals and results in improved vasoreactivity, even spasmolysis and a permanent reduction of the vascularlesion by inhibition of smooth muscle cell proliferation.

Methods

A. Cell Cultures

Porcine primary aortic vascular smooth muscle cell (PAVSMC) were isolated from porcine aortic arch by an explant method and grown in medium 199 (Gibco Life Sciences) with 20% fetal bovine serum. PAVSMC cultures before passage 5 were used throughout the experiments and were maintained in a subconfluent state. 3T3, 293 and A549 cell line were obtained from ATCC (Manassas, Va.) and cultured as recommended.

B. Gene Targeting

Human heme oxygenase 1 was amplified by reverse transcription polymerase chain reaction from human placental total RNA (5'primer GCGGAGCCAGCACGAACGA (SEQ ID NO:3); 3'primer GTGCCCACGGTMGGMGC (SEQ ID NO:4)) generating a 963 bp fragment encoding full length HO1 and sequenced by the dideoxy chain termination method. Total cellular human RNA was extracted by acid-guanidinium using Trizol® (GIBCO BRL, Gaithersburg, Md.). The adenoviral shuttle plasmid was constructed by subcloning HO1, under control of a cytomegalovirus promoter and the immediate-early CMV enhancer (pcDNA3, Invitrogen), into a pAd-BgI II shuttle plasmid harboring the adenoviral 0–1 and the 9–16 map unit. Recombinant E1A–E3 deficient adenoviruses encoding for human HO1 or nuclear-tagged β-galactosidase under the control of cytomegalovirus promoter were constructed by homologous recombination in 293 cells (ATCC, Manassas, Va.).

Individual plaques were isolated and recombinant viruses were propagated to at least two rounds of plaque assay. Viruses were eventually purified in a double-banded cesium chloride gradient and viral titer was determined by optical densimetry (260 nm) and standard plaque assay using 293 cells. Wild type contamination was assessed using standard plaque assay using A549 cells, quantitative polymerase chain reaction analysis of the purified virus stocks and southern blot analysis for E1A genomic DNA. Viral stocks containing less than 1 pfu wild type adenovirus per $1 \times 10^9$ pfu recombinant adenovirus were used throughout the experiments.

In the in vitro experiments, cultured 3T3 and PAVSMC were incubated with recombinant adenovirus for 2 hours in low serum conditions (Ml 99/3%FCS) and subsequently incubated for at least 24 hours at normal serum conditions. In order to synchronize the cells in G1/G0, cells were then transferred to serum free conditions (0.2% BSA). After 24 hours, fetal bovine serum was added to the cultures to initiate cell cycle progression. In all experiments, moi was calculated as plaque forming units per cell. Gene transfer efficiency was analyzed by parallel Ad-ntLacZ infection. β-galactosidase expression was analyzed by fixing the cells in 0.5% glutaraldehyde and staining with X-gal for 1 hour at 37° C. The percentage of infected cells was determined by counting the stained and total number of cells in 4 random microscopic fields (200 ×). Recombinant adenovirus without a foreign gene (Ad-ΔE1A) and buffer were included as controls.

C. Immunohistochemistry

Immunohistochemistry was performed on formalin fixed, paraffin-embedded tissue using an ABC immunoperoxidase (BrdU) and alkaline phosphatase (HO1) protocol. 5 μm transverse sections were placed on poly-L-lysine-coated slides, deparaffinized in xylene and rehydrated in ethanol and PBS. Primary antibodies were diluted in PBS with 1% BSA and 4% normal goat serum and applied on the slides for 24 hours at 4° C. in a moisturized chamber. A rabbit polyclonal anti-human HO1 antibody (1:300; AffinitiResearch Products, Mamhead Castle, UK) and a mouse monoclonal alkaline phosphatase-conjugated anti-BrdU antibody (1 U/ml, Boehringer Mannheim, Germany) were used as primary antibodies. After several washes with PBS, a peroxidase labeled conjugate (Vector Labs) for 30 min at room temperature and 3'3-diaminobenzidine with nickel chloride for 20 min at room temperature to yield a dark brown reaction product.

For peroxidase labeling, a biotinylated goat anti-rabbit secondary antibody (1:500, Vector Labs) was applied on the slides for 3 hours at 4° C, followed by avidin-biotin-streptavidin conjugate (Vector Labs) for 30 min at room temperature and alkaline phosphatase substrate (RED KITO, Vector Labs) for 20 min to yield a purple-red reaction product. Methyl green was used as a nuclear counter stain. Control samples were incubated with purified rabbit serum and did not result in any non-specific staining. Cell pellets of 293 cells transfected with a HO1 expression vector or a empty expression vector by calcium phosphate precipitation, served as a positive and negative control during the studies. Immunostaining was completely abolished by preabsorption of the antibody with the HO1 synthetic peptide (1 mg/ml, Affiniti Labs).

D. Immunoblot Analysis of HO1 Expression in PAVSMC

Western blot analysis was performed on whole cell lysates by incubating trypsinized cell cultures or homogenized arterial samples in lysis buffer (50 mM Tris pH 7.5, 250 mM NaCl, 2 mM EDTA, 10% glycerol, 0.1% NP40) with additional protease inhibitors (0.5 mM PMSF, 10 μg/ml aprotonin, 10 μg/ml leupeptin, 1 mM NaF, 0.1 mM $Na_3VO_4$, 1 mM DTT). Cellular debris was spun down at 16000 $g_{av}$ for 10 min, and protein concentration was determined by Bradford analysis. Samples were boiled for 5 min and 25 μg protein per lane was loaded on a 12% denaturing SDS-PAGE polyacrylamide gel. The gel was blotted on PVDF membrane and incubated with a rabbit polyclonal anti-heme oxygenase-1 antibody (Affinity Lab, UK; 1:500), a secondary donkey anti-rabbit horseradish-labeled antibody (Amersham Life Sciences, Arlington Heights, Ill.; 1:5000) and Supersignal® (Pierce) as substrate.

E. Cell Cycle Progression Analysis by Flow Cytometry and [3H]thymidine Incorporation.

Porcine aortic primary SMC were seeded at $2.5 \times 10^5$ cells per p100 plate (10% confluence). After 12 h, the VSMC were infected with recombinant adenovirus for 2 hours in M199 medium containing 3% FCS. The media was then changed to M199 containing 20% FCS for 24 h. Subsequently, the cultures were serum deprived for 24 hours (M199, 0.2% BSA), followed by reintroduction of FCS to 20% v/v with(out) the different heme oxygenase inhibitors (ZnPP IX; 10–100 μM), soluble guanylyl cyclase inhibitors and monophosphothioate inhibitors ((R)-p-bromoguanosine 3',5'-cyclic monophosphorothioate (Rp-8-BrcGMPS, 30 μM), (R)-p-bromoadenosine 3',5'-cyclic monophosphorothioate (Rp-8-BrcAMPS, 30 μM), Sp-8-(4-chlorophenylthio)-guanosine 3',5'-cyclic monophosphorothioate (Sp-8-pCPT-cGMPS, 30 μM), 1H-[1,2,4] oxadiazolo [4,3a] quinoxaline-1-one (ODQ, 3 μM), L-$N^G$-Nitroarginine methyl ester HCl (L-NAME, NOS inhibitor, 1 mM).

Cell number was determined every 12 hours using a haemacytometer at low power magnification and trypan blue 0.4% (Gibco BRL) to exclude apoptotic and necrotic cells. No differences in cell viability were observed after viral infection and 24 hours serum deprivation between control (noninfected or ΔE1A-Ad infected cells) and Ad-HO1 infected cultures as determined by trypan blue exclusion, numbers of non adherent cells after virus incubation and ANNEXIN-V-FLUOS-aided flow cytometry (Boehringer Mannheim).

Following G1/G0 arrest by mitogen deprivation, cells were transferred to M199 with 20% FCS and [$^3$H]thymidine (10 mCi/ml, NEN Life Science Products). After an incubation period of 24 h, [$^3$H]thymidine-treated cells were trypsinized and transferred to Whatmann filter paper. The samples were washed three times with 10% trichloric acid and twice with 100% ethanol. The filter papers were transferred to scintillation vials and measured by scintillation spectroscopy. Data are presented as means ± sem in counts per minute of [$^3$H]thymidine incorporated per well. [$^3$H]thymidine incorporation was normalized for cell number in the different experimental groups.

For assessment of cell cycle distribution, the cells were harvested, washed twice with phosphate-buffered saline (PBS), fixed in ice-cold 70% ethanol for 20 min and washed twice in ice cold PBS. The cells were then treated with 1 U of DNAase-free RNase per $1 \times 10^6$ cells for 20 min at 37° C. and resuspended in 0.03 mg/ml propidium iodide. DNA content was analyzed by flow cytometry using a FACSCAN model (Becton Dickinson).

F. Cyclic Nucleotide Immunoassays

Levels of cGMP were quantified using a commercial competitive immunoassay (Biomol, Plymouth Meeting Pa., USA) according to the manufactory protocol. In short, primary low passage vsmc cultures were plated in 35 mm plates to a density of $5 \times 10$ cell per well and maintained at M199 with 20% FCS for 48 hours. The cultures were infected with the recombinant Ad-HO1, ΔE1A-Ad virus or PBS, and incubated for 24 hours in M199 with 20% FCS. Thirty minutes prior to cGMP analysis, FePP IX (heme chloride, Sigma Chemical, St. Louis, Mo.) was added to the cultures as a substrate to 5 mM. For analysis of cGMP content, cells were treated with 300 μl 0.1 N HCl after removal of media. The cell suspension was collected, spun down to remove cellular debris at $600 \times g_{av}$ and applied to a 96 well plate coated with the goat anti-rabbit IgG antibody. In the assay, cGMP in the samples compete with an alkaline phosphatase conjugated cGMP for binding to a rabbit anti-cGMP antibody during a 2 hour incubation period at room temperature. The wells are then washed, incubated with substrate (p-nitrophenyl phosphate) for an hour yielding a yellow discoloration, and read at 405 nm by optical density (correction at 490 nm). All measurements were carried out in duplo.

G. Porcine Iliofemoral Balloon Injury and in vivo Vascular Gene Transfer in Pigs and Rats Anesthetized domestic Yorkshire pigs (12–15 kg) underwent sterile surgical exposure of the iliofemoral arteries by laparotomy. A double balloon catheter (CR Bard Inc) was inserted into the iliofemoral artery as described previously (Nabel et al., Science, 249:1285–1288,1990). The proximal balloon was inflated to 500 mmHg for 5 min. The intersection between the two balloons is then positioned over the injured artery and both proximal and distal balloons are inflated. 1cc of $1 \times 10^{12}$ part/ml recombinant virus is instilled into the isolated arterial segment between the balloons for 20 min at 150 mmHg. Animals were sacrificed 4, 7, 14, 21 and 60 days later. Pigs designated for analysis of vascular cell proliferation (n=4) received an intravenous injection of BrdU (25 mg/kg) 1 hour prior to sacrifice. For histological analysis, the arteries were perfused with 10% buffered formalin at 100 mmHg and placed in 10% formalin for an additional 4 hours, followed by 70% ethanol for 18 hours and paraffin embedded. Neointimal and medial cross sectional surface areas of injured arteries were analyzed by computer assisted morphometry of four adjacent sections covering the complete vascular lesion and site of gene transfer. Analysis was performed by investigators blinded to the individual experimental groups.

H. Vasoreactivity Analysis

Yorkshire pigs underwent vascular gene transfer into the iliofemoral arteries using $1 \times 10^{12}$ part/ml Ad-HO1 or ΔE1A-Ad as described. At 4 days after surgery, iliofemoral arteries were removed, cleaned under a dissecting microscope in PSS buffer (NaCl 130; KCl 4.7; $KH_2PO_4$ 1.18; $MgSO_4$-$7H_2O$ 1.17; $CaCl_2$—$H_2O$ 1.6; $NaHCO_3$ 14.9; dextrose 5.5; $CaNa_2$ EDTA 0.03g/L), cut into rings 2 mm in length and mounted in organ chambers containing PSS aerated with 95% $O_2$ and 5% $CO_2$ for measurement of isometric force development. Endothelial integrity was tested by exposure of the rings to acetylcholine in phenylephrine-contracted segments. After equilibration under a constant passive force (~6g) for 60 min, cumulative dose-response curves to phenylephrine ($10^{-9-10^{31.5}}$ M) were recorded in the presence of indomethacin ($10^{-5}$ M) and L-Nω-nitro-arginine ($10^{31.5}$ M), and analyzed using MACLAB 400 (AD Instruments, Milford, Mass.). The organ baths were washed out and the tissues were allowed to relax. A HO1 specific inhibitor (ZnPP IX, 20 µM) was then added to the baths and incubated for 1 hour. The phenylephrine vasoconstriction curves were recorded again under HO1 inhibition. The contractions elicited were expressed as percentage of maximal contraction or mNewtons of force.

1. Statistical analysis

Experimental data was analyzed using a one-way analysis of variance (ANOVA) followed by supplemental modified Student's-t-tests. Cumulative phenylephrine dose-response curves were analyzed using an analysis of variance for repeated measures (MANOVA). Differences were considered significant at $P<0.05$.

Materials

Zinc(ll)protoporphyrin IX was purchased from Sigma (St. Louis, Mo.). Fetal calf serum and M199 were derived from Gibco BRL. The monophosphotioate inhibitors of cyclic-nucleotide-dependent protein kinases (Rp-8-BrcGMPS, Rp-cAMPS), the cGMP analog (Sp-8-pCPT-cGMPS) and soluble guanylyl inhibitor (ODQ) were from Biomol (Plymouth Meeting, Pa.). H89 was obtained from Calbiochem. [$^3$H]Thymidine was purchased from New England Nuclear Life Sciences Products (Boston, Mass.). All other reagents were from Sigma Chemical (St. Louis, Mo.) or Fisher Biochemicals (Pittsburgh, Pa.).

What is claimed is:

1. A method for inhibiting vascular smooth muscle cell proliferation, comprising contacting the cell in-vitro with an isolated nucleic acid encoding a heme oxygenase 1 gene, wherein expression of the heme oxygenase 1 gene inhibits proliferation of the cell.

2. The method of claim 1, wherein said nucleic acid is a eukaryotic expression vector.

3. The method of claim 2, wherein said eukaryotic expression vector is a viral vector.

4. The method of claim 3, wherein said viral vector is an adenoviral vector.

5. The method of claim 4, wherein said adenoviral vector is Ad-HO1.

6. The method of claim 2, wherein said eukaryotic expression vector encoding said heme oxygenase I gene is complexed with a nonviral vector.

7. The method of claim 6, wherein said nonviral vector is a liposome.

8. A method of inhibiting vascular smooth muscle cell proliferation in-vivo, comprising locally administering to the patient an isolated nucleic acid encoding a heme oxygenase 1 gene, wherein expression of the heme oxygenase 1 gene inhibits proliferation of a vascular smooth muscle cell.

9. The method of claim 8, wherein administration is through a catheter.

10. The method of claim 9, wherein the catheter is selected from the group consisting of injection catheters, balloon catheters, double balloon catheters, microporous balloon catheters, channel balloon catheters, infusion catheters, and perfusion catheters.

11. The method of claim 8, wherein the administration is by a device selected from the group consisting of hypodermic needles, needle injection catheters, jet injectors, coated stents, bifurcated stents, vascular grafts, stent grafts, and coated wire coils.

12. The method of claim 11, wherein the nucleic acid coats the device.

13. The method of claim 12, wherein the nucleic acid is contained within a recombinant cell.

14. The method of claim 13, wherein the recombinant cell is an endothelial cell.

15. A medical device comprising an isolated nucleic acid encoding HO1.

16. A kit comprising a medical device of claim 15.

17. The medical device of claim 15, wherein the device is a catheter.

18. A kit comprising a medical device of claim 17.

19. The medical device of claim 17, wherein the catheter is selected from the group consisting of injection catheters, balloon catheters, double balloon catheters, microporous balloon catheters, channel balloon catheters, infusion catheters, and perfusion catheters.

20. A kit comprising a medical device of claim 19.

21. The medical device of claim 15, wherein the medical device is selected from the group consisting of hypodermic needles, needle injection catheters, jet injectors, coated stents, bifurcated stents, vascular grafts, stent grafts, and coated wire coils.

22. A kit comprising a medical device of claim 21.

23. The medical device of claim 21, wherein the nucleic acid coats the device.

24. A kit comprising a medical device of claim 23.

25. The medical device of claim 23, wherein the nucleic acid is contained within a recombinant cell.

26. A kit comprising a medical device of claim 25.

27. The medical device of claim 25, wherein the recombinant cell is an endothelial cell.

28. A kit comprising a medical device of claim 27.

* * * * *

SEQUENCE LISTING

<160> NUMBER OF SEQ ID NOS: 4

<210> SEQ ID NO 1
<211> LENGTH: 1550
<212> TYPE: DNA
<213> ORGANISM: Homo sapiens

<400> SEQUENCE: 1

```
tcaacgcctg cctcccctcg agcgtcctca gcgcagccgc cgcccgcgga gccagcacga      60
acgagcccag caccggccgg atggagcgtc cgcaacccga cagcatgccc caggatttgt     120
cagaggccct gaaggaggcc accaaggagg tgcacaccca ggcagagaat gctgagttca     180
tgaggaactt tcagaagggc caggtgaccc gagacggctt caagctggtg atggcctccc     240
tgtaccacat ctatgtggcc ctggaggagg agattgagcg caacaaggag agcccagtct     300
tcgcccctgt ctacttccca gaagagctgc accgcaaggc tgccctggag caggacctgg     360
ccttctggta cgggccccgc tggcaggagg tcatccccta cacaccagcc atgcagcgct     420
atgtgaagcg gctccacgag gtggggcgca cagagcccga gctgctggtg gcccacgcct     480
acacccgcta cctgggtgac ctgtctgggg gccaggtgct caaaaagatt gcccagaaag     540
ccctggacct gcccagctct ggcgagggcc tggccttctt caccttcccc aacattgcca     600
gtgccaccaa gttcaagcag ctctaccgct cccgcatgaa ctccctggag atgactcccg     660
cagtcaggca gagggtgata gaagaggcca agactgcgtt cctgctcaac atccagctct     720
ttgaggagtt gcaggagctg ctgacccatg acaccaagga ccagagcccc tcacgggcac     780
cagggcttcg ccagcgggcc agcaacaaag tgcaagattc tgccccgtg gagactccca     840
gagggaagcc cccactcaac acccgctccc aggctccgct tctccgatgg gtccttacac     900
tcagctttct ggtggcgaca gttgctgtag ggcttatgc catgtgaatg caggcatgct     960
ggctcccagg gccatgaact ttgtccggtg gaaggcttc tttctagaga gggaattctc    1020
ttggctggct tccttaccgt gggcactgaa ggctttcagg gcctccagcc ctctcactgt    1080
gtccctctct ctggaaagga ggaaggagcc tatggcatct tccccaacga aaagcacatc    1140
caggcaatgg cctaaacttc agaggggggcg aaggggtcag ccctgccctt cagcatcctc    1200
agttcctgca gcagagcctg gaagacaccc taatgtggca gctgtctcaa acctccaaaa    1260
gccctgagtt tcaagtatcc ttgttgacac ggccatgacc actttccccg tgggccatgg    1320
caatttttac acaaacctga aaagatgttg tgtcttgtgt ttttgtctta tttttgttgg    1380
agccactctg ttcctggctc agcctcaaat gcagtatttt tgttgtgttc tgttgttttt    1440
atagcagggt tggggtggtt tttgagccat gcgtgggtgg ggagggaggt gtttaacggc    1500
actgtggcct tggtctaact tttgtgtgaa ataataaaca acattgtctg                1550
```

```
<210> SEQ ID NO 2
<211> LENGTH: 288
<212> TYPE: PRT
<213> ORGANISM: Homo sapiens

<400> SEQUENCE: 2

Met Glu Arg Pro Gln Pro Asp Ser Met Pro Gln Asp Leu Ser Glu Ala
 1               5                  10                  15

Leu Lys Glu Ala Thr Lys Glu Val His Thr Gln Ala Glu Asn Ala Glu
                20                  25                  30

Phe Met Arg Asn Phe Gln Lys Gly Gln Val Thr Arg Asp Gly Phe Lys
            35                  40                  45

Leu Val Met Ala Ser Leu Tyr His Ile Tyr Val Ala Leu Glu Glu Glu
        50                  55                  60

Ile Glu Arg Asn Lys Glu Ser Pro Val Phe Ala Pro Val Tyr Phe Pro
65                  70                  75                  80

Glu Glu Leu His Arg Lys Ala Ala Leu Glu Gln Asp Leu Ala Phe Trp
                85                  90                  95

Tyr Gly Pro Arg Trp Gln Glu Val Ile Pro Tyr Thr Pro Ala Met Gln
            100                 105                 110

Arg Tyr Val Lys Arg Leu His Glu Val Gly Arg Thr Glu Pro Glu Leu
        115                 120                 125

Leu Val Ala His Ala Tyr Thr Arg Tyr Leu Gly Asp Leu Ser Gly Gly
    130                 135                 140

Gln Val Leu Lys Lys Ile Ala Gln Lys Ala Leu Asp Leu Pro Ser Ser
145                 150                 155                 160

Gly Glu Gly Leu Ala Phe Phe Thr Phe Pro Asn Ile Ala Ser Ala Thr
                165                 170                 175

Lys Phe Lys Gln Leu Tyr Arg Ser Arg Met Asn Ser Leu Glu Met Thr
            180                 185                 190

Pro Ala Val Arg Gln Arg Val Ile Glu Glu Ala Lys Thr Ala Phe Leu
        195                 200                 205

Leu Asn Ile Gln Leu Phe Glu Glu Leu Gln Glu Leu Leu Thr His Asp
    210                 215                 220

Thr Lys Asp Gln Ser Pro Ser Arg Ala Pro Gly Leu Arg Gln Arg Ala
225                 230                 235                 240

Ser Asn Lys Val Gln Asp Ser Ala Pro Val Glu Thr Pro Arg Gly Lys
                245                 250                 255

Pro Pro Leu Asn Thr Arg Ser Gln Ala Pro Leu Leu Arg Trp Val Leu
            260                 265                 270

Thr Leu Ser Phe Leu Val Ala Thr Val Ala Val Gly Leu Tyr Ala Met
        275                 280                 285

<210> SEQ ID NO 3
<211> LENGTH: 19
<212> TYPE: DNA
<213> ORGANISM: Artificial Sequence
<220> FEATURE:
<223> OTHER INFORMATION: Description of Artificial Sequence:5' primer

<400> SEQUENCE: 3
gcggagccag cacgaacga                                              19

<210> SEQ ID NO 4
<211> LENGTH: 19
<212> TYPE: DNA
```

-continued

```
<213> ORGANISM: Artificial Sequence
<220> FEATURE:
<223> OTHER INFORMATION: Description of Artificial Sequence:3' primer

<400> SEQUENCE: 4
gtgcccacgg taaggaagc                                                19
```